United States Patent [19]
Champon

[11] Patent Number: 6,051,233
[45] Date of Patent: Apr. 18, 2000

[54] ALL NATURAL SOIL TREATMENT AND INSECTICIDE COMPOSITION CONTAINING PLANT EXTRACT HEAT COMPONENTS

[76] Inventor: Louis S. Champon, 351 S. Cypress Rd. Suite 400, Miami, Fla. 33060

[21] Appl. No.: 08/961,673

[22] Filed: Oct. 31, 1997

[51] Int. Cl.[7] .......................... A61K 35/78; A01N 25/34; A01N 25/00
[52] U.S. Cl. ........................ 424/195.1; 424/403; 424/404; 424/405; 424/919; 514/655; 514/783
[58] Field of Search .................................. 424/195.1, 403, 424/404, 405, 919; 514/655, 783

[56] References Cited

U.S. PATENT DOCUMENTS

| | | | |
|---|---|---|---|
| 4,999,187 | 3/1991 | Vernon | 424/705 |
| 5,145,675 | 9/1992 | Won | 424/78.31 |
| 5,188,822 | 2/1993 | Viccaro et al. | 424/52 |
| 5,240,708 | 8/1993 | Plummer et al. | 424/405 |
| 5,416,075 | 5/1995 | Carson et al. | 514/23 |
| 5,466,459 | 11/1995 | Wilson | 424/407 |
| 5,525,597 | 6/1996 | Hainrihar et al. | 514/75 |
| 5,645,845 | 7/1997 | Neuman et al. | 424/405 |

*Primary Examiner*—Leon B. Lankford, Jr.
*Assistant Examiner*—Christopher R. Tate
*Attorney, Agent, or Firm*—Oltman, Flynn & Kubler

[57] ABSTRACT

This invention encompasses a chemical composition comprising heat components, mustard oil, lemon extract, vegetable oil, and surfactants. The invention also encompasses a method of using said chemical composition as a soil treatment, insecticide, commodity fumigant, and structural fumigant.

7 Claims, No Drawings

ALL NATURAL SOIL TREATMENT AND INSECTICIDE COMPOSITION CONTAINING PLANT EXTRACT HEAT COMPONENTS

BACKGROUND OF THE INVENTION

1. Field of the Invention

The invention relates to the fields of soil treatment, insecticides, commodity fumigation, and structural fumigation.

Before crops are planted, the soil is chemically treated. Soil treatments sterilize the soil, killing the vast majority of organism. By eliminating pests and disease, crop yields are increased.

Insecticides are used to control insect populations in areas such as crops, homes, and food storage areas.

Commodity fumigation is the sterilization of food during transportation and storage. Most commodities must be fumigated during importation and quarantine.

Structural fumigation is the sterilization of buildings. Structural fumigation also includes sterilizing a site of future construction.

2. Description of the Related Art Including Information Disclosed under 37 CFR 1.97 and 1.98

Currently, the most effective substance for soil treatment is methyl bromide. Methyl bromide is used in the control of pest insects, nematodes, weeds, pathogens, and rodents. In the United States, about 27,000 tons of methyl bromide is used annually in agriculture, primarily for soil fumigation, as well as for commodity and quarantine treatment, and structural fumigation. Globally, about 76,000 tons of methyl bromide are used each year.

When used as a soil treatment, methyl bromide is injected into the soil at a depth of 12 to 24 inches before a crop is planted. This will effectively sterilize the soil, killing the vast majority of soil organisms. Immediately after the methyl bromide is injected, the soil is covered with plastic tarps that hold most of the methyl bromide in the soil. The tarps are removed 24 to 72 hours later.

After the tarps are removed, much of the methyl bromide leaves the soil. The EPA estimates that about 50% to 95% of the methyl bromide in the soil eventually enters the atmosphere.

While methyl bromide in large doses can result in damage to the human nervous system and respiratory system, the greatest danger poised by methyl bromides is the damage to the ozone layer. According to the 1994 Assessment of Ozone Depletion, the Ozone Depletion Potential (ODP) of methyl bromide has been assessed to be 0.6. This makes the ODP of the methyl bromide fifty times more effective at destroying ozone than CFC's on a per molecule basis.

According to the Clean Air Act (1990 Amendments), all substances with an ODP of 0.2 or greater are to be phased out in the United States. This means that methyl bromide is being phased out. Starting Jan. 1, 2001, the EPA will prohibit the production and importation of methyl bromide in the United States. Other nations such as the Netherlands and Denmark will ban the use of methyl bromide in 1998. In addition, 160 countries have signed the Montreal Protocol, a treaty calling for the levels of ozone-depleting chemicals to be frozen at 1991 levels. Finally, the EPA is lobbying for nations to stop using methyl bromide all together.

In light of the environmental problems with methyl bromide, and the continuing need for a soil treatment, an environmentally safe chemical alternative has been sought.

One broad group of naturally occurring products are plants with heat components such as peppers.

In the prior art, other uses and composition involving the heat components, mustard oil, and citrus extracts have been suggested. These compositions never combine all of the active ingredients. In addition they do not provide methods of using a composition made by combining heat components, mustard oil, and citrus extracts.

In U.S. Pat. No. 4,455,304, Yaralian disclosed a composition for repelling animals having capsicum and finely divided garlic along with other inert ingredients. This patent only involves compositions made with garlic together with cayenne pepper, a pungent pepper fruit borne by plants of the genus Capsicum. The patent also discloses a method of using said composition. The patent makes no mention of capsaicin with allyl isothiocyante, and lemon oil, in addition to inert ingredients. The disclosed method did not involve soil treatment.

In U.S. Pat. No. 4,440,783, Downing discloses a composition for warding off of animals such as racoons, dogs and the like from garbage. The composition combines isothiocyanates with lemon grass oil. The patent does not disclose the use of capsaicin with the other ingredients. The composition does not involve a wetting agent (surfactant) and the method does not involve soil treatment.

In U.S. Pat. No. 5,525,597, Hainrihar,et. al., disclose an insecticide that combines normally-employed insecticides along with an activity-enhancing amount of capsaicin. The active ingredient in this formulation is the insecticide. The capsaicin ingredient used only enhances the active ingredient and is not active itself.

In U.S. Pat. No. 5,240,708, Plumer, et. al., disclose a method for preparing a solution that can be used to discourage spiders, insects, and the like. The disclosed composition involve the use of capsicum agents in conjunction with soaps, acetic acid, and anise. The compositions disclosed are incompatible with soil treatment because the soaps, acetic acid, and levels of capsicum in the disclosed composition would also kill any plants that would be planted in the soil.

In U.S. Pat. No. 5,674,496, Etscorn discloses a method of extracting capsaicinoids from peppers and then incorporating the extract in polymers. Etscorn never discloses combining capsaicinoids with other active ingredients. In addition, the method of using the composition as soil treatment is not contemplated by Etscorn.

SUMMARY OF THE INVENTION

The invention encompasses a chemical composition and a method of treating soil using the chemical composition.

The chemical composition is environmentally safe. The active ingredients in the composition are all plant extracts. In addition, all of the ingredients used are considered safe for use with food by the Food and Drug Administration (FDA). The result is a composition that is safe for the environment and for use in growing food.

The first group of active ingredients involve the group compounds responsible for the "heat component" of taste comprising: capsaicin, ginger oil, black pepper oil, ginger oleo resin, black pepper oleo resin, capsaicinoids, cassia oil, cinnamon leaf oil, cinnamon bark oil, cinnamic aldehyde, bitter almond oil, and benzaldehyde. The heat component acts to burn out insects, disease, toxins, and other pests.

The next group of active ingredients are the mustard oils. The types of mustard oil comprise horseradish oil and allyl isothiocyanate. The mustard oil ingredients work by breaking down into cyanide containing compounds.

The first inert ingredient is from the group of citrus extracts comprising lemon oil, d-limonene, citronella oil, litsea cubeba, orange terpenes, citrus terpenes, lemon terpenes, lime terpenes, lime oil, orange oil, mandarin oil, and citral. Although considered inert by the EPA, citrus extracts still have sanitizing effect and work to sanitize different targets than the heat components and mustard oils.

The second inert ingredient is vegetable oil. Any vegetable oil will work. Examples of suitable vegetable oils are soybean oil, corn oil, sweet almond oil, olive oil, avocado oil, and safflower oil.

A final inert ingredient is a surfactant that acts as a wetting agent. The wetting agent helps during the dilution of the chemical composition in water. The wetting agent also helps the chemical composition saturate the soil. A food grade surfactant should be used due to the composition's use as a soil treatment. An example of a suitable surfactant is polysorbate 80.

The amount of active ingredients is governed by two opposing factors. First, enough active ingredient must be present so that the composition is effective. Second, the soil cannot contain too much active ingredient otherwise the composition will not only prevent pests; it will prevent the desired plants as well.

The amount of surfactant is that necessary to wet fully the treated soil when the first dosage of composition is applied. This amount may change with soil composition and crop type.

The balance of the composition is completed with vegetable oil.

The range of weight percentages of ingredients necessary to create efficacious composition are the following:

| | |
|---|---|
| Heat component | 2–15% |
| Mustard oil | 2–15% |
| Citrus extract | 5–80% |
| Surfactant | 10% |
| Vegetable Oil | 0–81% |

The chemical composition that is made out combining the heat component, mustard oil, and citrus extract have enhanced qualities when combined. First a chemical composition that includes all three acts as a "broad spectrum" treatment. Broad spectrum means that the one composition is effective at eliminating most diseases and pests. A broad spectrum composition has the advantage of only one application being necessary to treat an area. When narrow spectrum compositions are used, a number of narrow-spectrum applications must be made in order to protect against all types of disease and pests. Finally, as a replacement for Methyl Bromide, a chemical composition must be broad spectrum. Practices, procedures, and dispensing methods are all currently set for methyl bromide, a broad-spectrum treatment.

In addition, when the ingredients are combined together and applied, the combined chemical composition is more efficacious than the sum of the individual parts. The chemical components not only have their usual action, they also make diseases and pests more susceptible to the other components.

The invention also encompasses several methods for the treatment of soil. The method involves diluting the concentrated solution in water. The diluted solution is then sprayed into the ground to a depth of 12 to 24 inches. The amount sprayed is the quantity necessary to saturate the soil. This amount is between 1%–20% by weight of the soil being treated. The amount depends on the type of soil being treated and the crop being grown.

The above described method of treating soil can be accomplished by injecting several types of plant extracts. First, the method can be accomplished by injecting vegetable extracts containing a heat component. Second, the method can be accomplished by injecting capsaicin-containing extracts. Third, the method can be conducted using a chemical composition comprising: a heat component, mustard oil, citrus extract, surfactant, and vegetable oil.

The invention also encompasses a method for structural and commodity fumigation. Structural fumigation involves the treatment of buildings to remove pests and insects. Structural fumigation also includes the treatment of soil before a building's foundation is placed upon it. Commodity fumigation is the removal of pests, insects, and disease from food that is being imported, quarantined, or stored. An important consideration in commodity fumigation is that the treated product will be consumed ultimately.

The method of structural and commodity fumigation involves diluting the concentrated chemical composition in water. Then compressed air is used to vaporize the concentrated liquid. The vaporized chemical composition is pumped into the treated area. Typically, the treatment is made in a closed area so that the chemical composition is not allowed to dissipate. By holding the chemical composition in the treated areas, the chemical composition is given enough time to act.

The invention also encompasses a method of using the composition as an insecticide. To use the composition as an insecticide the concentrated composition is diluted in water. The diluted chemical composition is then applied to the product. Preferably, the composition is added before infestation. However, if the product is already infested, the dilute chemical composition can be added with an increasing concentration depending on the level of infestation.

DESCRIPTION OF THE PREFERRED EMBODIMENTS

The invention encompasses a chemical composition usable for the treatment of soil. In its preferred embodiment, the composition has the following ingredients:

| | |
|---|---|
| Capsaicin and related capsaicinoids (in capsicum oleoresin) | 4.94% |
| Allyl isothiocyanate (in food grade Mustard Oil) | 4.43% |
| Lemon extract | 40.00% |
| Soybean oil | 32.64% |
| Polysorbate 80 (Tween 80 food grade) | 10.0% |
| Capsicum oleoresins (less active ingredients | 7.99% |

The preferred method of using the composition is to dilute it to 5% or 10% by weight in water. The dilution depends on the type of soil and crop. The dilute composition containing solution is then added to the soil. The amount to be added is the quantity necessary to saturate the soil. In sifted soil, the amount is 3.33% by volume of the soil.

An experiment was run to test the efficacy of the composition and the method. The composition and method were tested on sterile soil with added *Fusarium oxysporum f. sp.*

Chrysanthemi (hereinafter "F.o.c"), a widespread and destructive disease of horticultural crops. The density of F.o.c. in the soil was $1.1=10^6$ spores/$cm^3$. The concentrated composition was diluted with water to 1%, 5%, and 10% (by weight) aqueous solutions. Next, 5.0 ml of each dilution were added to 150 ml of infected soil. Population densities of F.o.c. were then taken at 1, 3, 7, 14, and 21 days after treatment. As controls, an untreated, infected sample was tested.

The results of the experiment are presented in the following table:

| Concentration of Soil Treatment | Elapsed Time (days) | | | | |
|---|---|---|---|---|---|
| Composition | 1 | 3 | 7 | 14 | 21 |
| Untreated | 5.40 | 5.45 | 5.48 | 5.40 | 5.32 |
| 1% | 5.26 | 5.43 | 5.22 | 5.30 | 5.40 |
| 5% | 5.02 | 1.91 | 1.85 | 3.59 | 4.49 |
| 10% | 3.32 | 1.31 | 1.55 | 2.00 | 3.02 |

The values in the table are mean values that are $log_{10}$ transformation of colony units (CFU per cubic centimeter ($cm^3$) of soil. Data represents the average of 2–6 experiments with three replications per treatment per experiment.

The results show that the composition significantly reduced the population density of F.o.c. compared to the untreated infected control soil when added to soil as either a 5% or 10% aqueous emulsion: the soil populations of F.o.c. were the lowest between 3 and 7 days.

The preferred embodiment of a method for structural and commodity fumigation follows: diluting the concentrated chemical composition to ten percent (10%) by weight in water; pressurizing the dilute chemical composition with air forcing the chemical composition into a gaseous state; filling the treatment area with the gaseous chemical composition; keeping the treated area closed for a period long enough that chemical composition can act.

The following is the preferred embodiment for a method of killing insects with the chemical composition preferred embodiment. The concentrated chemical composition is diluted according to the following table, depending on the level of infestation and the amount of diluted product needed, and mix amount needed.

| Level of Insect Infestation | Amount of Diluted Product (Gallons) | | |
|---|---|---|---|
| | 1 | 20 | 200 |
| Normal | 1.5 oz. | 30 oz. | 300 oz. |
| Heavy | 2.4 oz. | 48 oz. | 480 oz. |

Once diluted, the method of applying the mixture can be by hand, ground machine, or aerially. When applying by hand, to obtain maximum benefits, apply every 7 to 10 days before infestation begins. If infestation is present, apply 1½ oz. of chemical composition concentrate per gallon of water every four to five days and increase to 3 oz. per gallon of water after ten days. Fruits and vegetables treated with the chemical composition may be thoroughly washed and eaten the same day as application.

The method of applying by ground machine or aerial application is to apply the diluted chemical composition at a rate of 20 gallons per acre.

When using the chemical composition as an insecticide, apply as a full coverage, making sure both sides of the leaves are covered. Apply during cool periods of the day. Apply as a preventative treatment prior to infestation. Make the first application at pollar emergence and repeat on a 10–14 day spray schedule to maintain the repelling effect. D o no apply prior to or during pollination as the chemical composition kills and repels bees, and, therefore, adversely affects pollination.

I claim:

1. A chemical composition for soil-sanitizing treatment comprising:

a heat component as an active ingredient wherein said heat component is a plant extract selected from the group consisting of capsaicin, ginger oil, black pepper oil, ginger oloe resin, black pepper oleo resin, capsaicinoids, cassia oil, cinnamon leaf oil, cinnamon bark oil, cinnamic aldehyde, and bitter almond oil;

a mustard oil as an active ingredient wherein said mustard oil is selected from the group consisting of horseradish oil and allyl isothiocyanate; and the following inert ingredients:

a citrus extract selected from the group consisting of lemon oil, d-limonene, citronella oil, litsea cubeloa, lime oil, orange oil, mandarin oil, lemon terpenes, lime terpenes, orange terpenes, citrus terpenes and citral;

a surfactant chosen from the group of food grade surfactants comprising polysorbate 80, and a vegetable oil selected from the group consisting of soybean oil, corn oil, sweet almond oil, olive oil, avocado oil, and safflower oil;

wherein the chemical composition comprises: by weight, 2–15% said heat component; by weight, 2–15% said mustard oil; by weight, 5–80% said citrus extract; by weight, about 10% said surfactant; with said vegetable oil forming the balance of the composition.

2. A method of sanitizing soil, which comprises: forming a diluted chemical composition solution by:

diluting a primary chemical composition with water, said primary chemical composition comprising:

by weight, 2–15% of a heat component; by weight, 2–15% of a mustard oil; by weight, 5–80% of a citrus extract; by weight, about 10% of a surfactant; with a vegetable oil forming the balance of the composition;

wherein said heat component is a plant extract selected from the group consisting of capsaicin, ginger oil, black pepper oil, ginger oloe resin, black pepper oleo resin, capsaicinoids, cassia oil, cinnamon leaf oil, cinnamon bark oil, cinnamic aldehyde, and bitter almond oil;

said mustard oil is selected from the group consisting of horseradish oil and allyl isothiocyanate;

said citrus extract is selected from the group consisting of lemon oil, d-limonene, citronella oil, litsea cubeloa, lime oil, orange oil, mandarin oil, lemon terpenes, lime terpenes, orange terpenes, citrus terpenes and citral;

said surfactant is chosen from the group of food grade surfactants comprising polysorbate 80; and said vegetable oil is selected from the group consisting of soybean oil, corn oil, sweet almond oil, olive oil, avocado oil, and safflower oil;

and applying said diluted chemical composition solution to the intended soil sanitation area.

3. The method as described in claim 2, wherein said primary chemical composition is diluted to ten percent (10%) by weight with water to form said diluted chemical composition solution.

4. The method as described in claim 2, wherein said chemical solution is applied by spraying 3.33% by volume diluted chemical composition solution to the soil to be treated.

5. The method as described in claim 2, wherein said diluted chemical composition solution is applied by using pressurized air to force the chemical solution into a gaseous state;

pumping the chemical solution in the gaseous state into a closed volume containing the soil to be sanitized; and retaining the chemical solution in the closed volume for an amount of time, thereby allowing the chemical solution to act.

6. A chemical composition for soil-sanitizing treatment comprising:

one or more heat components as active ingredients wherein said heat components are plant extracts selected from the group consisting of capsaicin, ginger oil, black pepper oil, ginger oleo resin, black pepper oleo resin, capsaicinoids, cassia oil, cinnamon leaf oil, cinnamon bark oil, cinnamic aldehyde, and bitter almond oil;

one or more mustard oils as active ingredients wherein said mustard oils are selected from the group consisting of horseradish oil and allyl isothiocyanate; and the following inert ingredients:

one or more citrus extracts selected from the group consisting of lemon oil, d-limonene, citronella oil, litsea cubeloa, lime oil, orange oil, mandarin oil, lemon terpenes, lime terpenes, orange terpenes, citrus terpenes and citral;

a surfactant chosen from the group of food grade surfactants comprising polysorbate 80, and one or more vegetable oils selected from the group consisting of soybean oil, corn oil, sweet almond oil, olive oil, avocado oil, and safflower oil;

wherein the chemical composition comprises:
      by weight, 2–15% said one or more heat components; by weight, 2–15% said one or more mustard oils; by weight, 5–80% said one or more citrus extracts; by weight, about 10% said surfactant; with said one or more vegetable oils forming the balance of the composition.

7. The chemical composition of claim 6 wherein the chemical composition comprises:

by weight, 4.94% capsaicin and related capsaicinoids;

by weight, 4.43% allyl isothiocyanate;

by weight, 40% lemon extract;

by weight, 32.64% soybean oil; and by weight, 10% polysorbate 80.

* * * * *